(12) United States Patent
Alexander

(10) Patent No.: US 7,380,941 B1
(45) Date of Patent: Jun. 3, 2008

(54) DEVICE AND METHOD FOR ASSISTING DEVELOPMENT OF AN INFANT'S VISUAL ACUITY AND FOR TRANSFERRING A MOTHER'S SCENT TO AN INFANTILE ENVIRONMENT

(75) Inventor: James G. Alexander, Harrodsburg, KY (US)

(73) Assignee: Mobil Mom, LLC, Harrodsbure, KY (US)

( * ) Notice: Subject to any disclaimer, the term of this patent is extended or adjusted under 35 U.S.C. 154(b) by 329 days.

(21) Appl. No.: 11/223,529

(22) Filed: Sep. 9, 2005

(51) Int. Cl.
*A61B 3/02* (2006.01)

(52) U.S. Cl. .............. 351/224; 351/203; 442/59; 215/11.6; 215/386

(58) Field of Classification Search ............... 351/203, 351/209, 210, 224; 604/385.7, 359; 442/59, 442/96; 215/11.6, 386, 392
See application file for complete search history.

(56) References Cited

U.S. PATENT DOCUMENTS

| | | | |
|---|---|---|---|
| 1,669,061 A | 5/1928 | Meltzer | |
| 2,522,381 A | 9/1950 | Kramer | |
| 3,065,944 A * | 11/1962 | Liebendorfer | 248/102 |
| 3,570,139 A | 3/1971 | Ladd et al. | |
| 4,283,011 A | 8/1981 | Spector | |
| 4,514,995 A | 5/1985 | Curtis | |
| 4,582,492 A | 4/1986 | Etter et al. | |
| 4,631,754 A | 12/1986 | Ryan | |
| 4,724,623 A | 2/1988 | Silverman | |
| 4,989,285 A | 2/1991 | Troncone et al. | |
| 5,052,057 A | 10/1991 | Fetner | |
| 5,423,711 A | 6/1995 | Dorland | |
| 5,813,866 A | 9/1998 | Maeda | |
| 6,112,749 A | 9/2000 | Hall et al. | |
| 6,247,178 B1 | 6/2001 | Bilda | |
| 6,626,536 B2 | 9/2003 | Mesplay | |
| 6,772,891 B1 | 8/2004 | Song | |
| 2002/0006455 A1 | 1/2002 | Levine | |
| 2003/0028168 A1 * | 2/2003 | Mesplay | 604/385.07 |

OTHER PUBLICATIONS

The Enfamil® Family of Formulas™ Baby Book © 1997, Mead Johnson & Company.

* cited by examiner

*Primary Examiner*—Timothy Thompson
(74) *Attorney, Agent, or Firm*—Kenneth F. Pearce

(57) ABSTRACT

A device for assisting the development of an infant's visual acuity and for transferring the mother's scent to an infantile environment. Smooth and supple fabric contacts an area of the mother's body for absorbing a portion of the mother's scent and is thereafter transferred and located in proximity with the infantile environment for venting the transferred scent about the infantile environment. Due to the device's contrasting colors, the training of the infant's visual acuity can be enhanced.

16 Claims, 7 Drawing Sheets

DEVICE AND METHOD FOR ASSISTING DEVELOPMENT OF AN INFANT'S VISUAL ACUITY AND FOR TRANSFERRING A MOTHER'S SCENT TO AN INFANTILE ENVIRONMENT

BACKGROUND OF THE INVENTION

1. Field of the Invention

In the most general sense, the present invention relates to devices that can be assimilated with an infantile environment, such as, incubators, cradles, cribs or bassinets. The invention is useful in hospital wards for newborns and premature babies as well as day care facilitates or other infantile environments. Due to the device's contrasting colors, the training of the infant's visual acuity can be enhanced. In conjunction with the contrasting colors, fabrics or other supple materials which can absorb and thereafter transfer a portion of the scent of the infant's mother to a location apart from the mother create another attribute of the invention. When the device is placed near the infantile environment, the mother's scent is vented about the infant's environment such that the infant's olfactory senses can be stimulated by the mother's scent without the mother being present.

2. Description of the Previous Art a) U.S. Pat. No. 5,423,711—Dorland enables a convertible body garment with odor absorbing properties and process of using the convertible body garment. The Dorland garment is formed from a rectangular piece of fabric (16) which may be made from naturally occurring materials or blends thereof, such as cotton and/or blends with man made materials which absorb perspiration or body secretions. A pair of removable straps (18) are attached to the elongated side (20) of the rectangular shaped garment. Pockets (32) are attached to the inner surface of the garment in proximity to the breasts or axillae. The pockets are defined by a loose weave designed to retain body order absorbing material. After the method's body odor has been absorbed, the garment (10) is attached to a crib's mattress (50). In another embodiment, the '711 garment is attached to an infant seat, carrier or swing. And Column 4, lines 23-44, teach, "In a preferred application of the invention, the use of body odor absorbing material attached to the inner surface of the garment enhances the absorbency of odor . . . A process of promoting bonding between a person and an infant in accordance with the invention includes wearing a garment in contact with at least the person's body, such as the torso, comprising a material which absorbs odor from the body and a fastening means for attaching the garment to the body for a time sufficient to retain the odor; and attaching the worn garment to a garment support with fastening means sufficiently close to the infant so that the infant may smell the retained odor for a time sufficient to promote bonding." By reference, the disclosure of the Dorland Patent is specifically incorporated into the current Application, and more particularly, the disclosure therein related to odor absorbing materials and the resultant olfactory bonding between infants and their mothers.

2) U.S. Pat. No. 6,112,749—Hall, et. al., discloses the use of an absorbent pad made of cotton, felt, paper, etc. that has been impregnated with an odor, preferably vanilla, that is pleasing to the infant. Application of moisture activates the odor dot on the baby bottle. In another embodiment, an odor ring rather than a dot is affixed to the baby bottle. The '749 device also enables a methods including greater consumption of liquids, as well as, enriching the olfactory environment of the bottle's user.

3) U.S. Pat. No. 4,283,011—Spector enables a scented sticker that can be applied to clothing. The Spector stickers are embedded with a volatile having the odor analogous to the shape of the sticker.

4) U.S. Pat. No. 4,989,285—Troncone, et al., teaches a security blanket, preferably 35 centimeters by 45 centimeters, constructed to feel like the amnion lining in which the baby resides before birth. The Troncone blanket has one side that is soft brushed flannel and a second side made of charmeuse satin.

5) U.S. Pat. No. 4,582,492—Etter, et. al., enables a behavioral modification method using microencapsulation of odors on a patch. Dominant and subservient odors are microencapsulated onto disks. When the subject's urge becomes so strong that he feels as if he is loosing control, the disk is scratched which releases the subservient odor. After a period of time, the subservient odor fades and the dominant pleasant odor becomes pervasive once again and the subject is rewarded for avoiding the bad habit.

6) U.S. Pat. No. 5,813,866—Maeda describes a bed sheet or a lap robe including a cloth chart for learning characters. A plurality of pieces and kinds of cloth in color are connected in a continuous manner along the circumference of the face of the learning chart so that beautiful feelings for infants and children are formed. Pieces (41), (42), (43), (44) and (45) are respectively red, green, yellow, brown and blue.

7) U.S. Pat. No. 3,570,139—Ladd, et al., enables an instructional apparatus for use in early child development. The Ladd book includes visual and chemical-odor producing stimuli that allow the child to associate the thing displayed with its aroma. The display sheets (28) include incentive means (14) that are integrated with the story line as well as illustrative material to encourage the student to operate the Ladd, et al., apparatus. For example, the '139 Patent teaches that the candy canes exemplified therein also smell like peppermint.

8) U.S. Pat. No. 5,199,842—Watt et al., describes a nursing scarf and enables a method of nursing an infant utilizing the scarf.

9) U.S. Pat. No. 6,247,178—Bilda enables a convertible, scent retaining garment blanket. Bilda utilizes a shirt with detachable sleeves. To practice of the '178 detachable shirt, the parent wears the shirt and then detaches the sleeves from the body of the shirt. Either one of the sleeves or the torso of the shirt is used as a baby blanket.

10) U.S. Published patent application No. 20020006455 A1—Levine describes a baby food selection and method. Levine utilizes scratch and sniff technology to incorporate food flavor and food odors onto food containers, cards, game pieces or toys. By smelling or tasting the flavor or scent imparted to the food containers, cards, game pieces or toys, the pre-speaking baby can indicate the preferred food.

11) U.S. Pat. No. 6,626,536 B2—Mesplay enables a device and method for assisting development of an infant's visual acuity and for transferring a mother's scent to an infantile environment. The Mesplay Description of the Preferred Embodiments, in part, reads:

FIG. 1 depicts a black side (32) of supple fabric (30) including an aperture (34) that can be hooked onto a projection of an infantile environment (not shown), thereby attaching supple factor (30) to the infantile environment. FIG. 2 discloses a neutral white side (38) of supple fabric (30) and aperture (34). FIG. 3 portrays device (30) where aperture (34) has received thread (42). However, those skilled in the art recognize that thread (42) can be sewn directly into supple fabric (30), thereby circumventing use of aperture (34). FIG. 4 exemplifies, device (30) suspended from canopy (44) of bassinet (40) by thread (42). In FIGS. 5-8, linear (FIG. 5) and other geometric black on white patterns (FIG. 6, polka dot; FIG. 7, rectangular or square; FIG. 8, triangular) are depicted. Importantly, those skilled in the art recognized the patterns could just as easily be white on black backgrounds. Moreover, practice of the present invention is not limited to patterns disclosed in FIGS. 5-8, but can easily accommodate other geometric patterns. And still in accordance with the present invention, the sides (not shown) opposite the geometric pattern sides (50, 52, 54 and 56) of supple fabric (30) are neutral, i.e., white, off-white, pastel beige, pastel yellow, pastel gray, pastel blue, pastel pink, to name a few of the plethora of neutral colors available for use. Additionally, opposite sides (not shown) can be composed of a backing separate from supple fabric (30), or it can be composed solely of supple fabric (30).

The '536 Patent appears to enable supple fabrics that have either a solid black side and a solid neutral or white side or a geometric black and while pattern on a first side of the fabric and a neutral solid colored second side. In accordance with Mesplay, the colors of the neutral side can be either white, off-white, pastel beige, pastel yellow, pastel gray, pastel blue or pastel pink. Mesplay appears to be silent regarding the use of black and white patterns on both sides of the fabric, a black and while pattern on a first side of the device and a pattern of other colors on the second side of the device or colors other than black and white utilized on each side of the '536 device.

12) U.S. Pat. No. 6,772,891—Song enables a confort grip bottle holder. The Song Detailed Description of the Drawings reads:

The bottle sleeve 100 includes an elastic portion 104 and a fabric portion 102. The elastic portion 104 is expandable to accept bottle 200. The elastic portion 104 then constricts around the bottle 200 to securely fasten the bottle sleeve 100 to the bottle 200. The elastic portion 104 can be manufactured from a variety of different materials including but not limited to, foam, rubber or an elastic fabric such as those used in the manufacture of athletic socks. The use of a variety of elastic materials does not detract from the spirit of the invention. The fabric portion 102 is attached to the elastic portion 104. In one disclosed embodiment, the fabric portion 102 is sewn together with the elastic portion 104. However, a wide variety of attachment schemes can be implemented without detracting from the spirit of the invention. The fabric portion 102 is made from a soft, scent absorbing fabric. The fabric portion 102 surrounds the nipple 106 of the bottle 200 such that the tip of the nipple 106 is accessible by an animal. The fabric portion 102, in one disclosed embodiment, can be manufactured in a donut shape with padding to provide a soft nuzzle area for an animal feeding from the nipple 106. The soft, scent absorbing fabric of the fabric portion 102 allows for the scent of the animal feeding from the bottle 200 to be absorbed so that the animal will recognize its own scent at subsequent feedings. This recognition will assist in later feedings. The claws of the animal on both the front and rear feet typically do not grasp a plastic or glass bottle such as those shown in FIG. 6. This causes difficulty in allowing the animal to nurse. However, the claws of the front and back feet can securely grip the elastic portion 104 and fabric portion 102 of the bottle sleeve 100 of the present disclosed embodiment.

Song requires an elastic member for enveloping the bottle that is connected to a ring like fabric portion that surrounds the nipple. The ring like fabric portion can absorb the mother animal's scent. Since the '891 Patent refers to "the claws of the animal on both the front and rear feet typically do not grasp a plastic or glass bottle," it appears that Song's device is directed toward animals other than humans. Song is silent regarding any assonance with the development of an infant's visual acuity or the transfer of the mother's scent to an infantile environment.

13) U.S. Pat. No. 4,514,995—Curtis, et al. enables a knit cover for a beverage container. The Curtis Summary of the Invention reads:

In order to prevent slippage from the hand when placed on a beverage container, an outwardly bulging hand engagable annular band is formed around the upper medial portion of the sleeve. This band is formed during the knitting of the sleeve and is produced by holding the stitch loops on one set of needles while knitting several courses of stitch loops on the other set of needles, and then again knitting on both sets of needles. The present knit cover also has a uniform bottom portion which is adapted to partially enclose the flat bottom of a beverage container which is slidably inserted in the sleeve. This bottom portion is formed by discontinuing the ribbed pattern and providing a non-elastic lower terminal edge opening. This lower opening has a diameter which is smaller than the upper opening, and the lower opening preferably does note stretch as much as the remainder of the sleeve when a container is inserted therein. This prevents the beverage container from slipping out of the lower end of the sleeve while at the seam time functioning as a coaster having a substantially uniform bottom portion, which, having no irregularities, is unlikely to cause the container to tip over and spill its contents. The knit cover may be economically formed on a circular knitting machine having two sets of needles and capable of knitting seamless tube or sleeve of rib fabric, preferably in a one-by-one rib pattern. This pattern is continued for approximately one and one half inches or twenty to thirty courses in a preferred embodiment, and then the needles knitting the inwardly facing stitch loops hold their stitch loops while the needles knitting the outwardly facing or plain stitch loops continue to knit for about three to eight courses, to form the outwardly bulging band. All needles then again knit and the rib pattern is continued to an overall length of between about six to seven inches. The diameter of the knit cover of the present invention is dependent in part upon yarn weight, the tension used, the diameter and gauge of the machine, and the number of stitch loops formed in each course. Working with a sport or worsted weight acrylic fiber yarn, and a one-by-one rib knit pattern, a machine provided with 60 needles produces an appreciate diameter for the knit cover. Yarn of acrylic fiber is preferred due to its inherent elasticity and heat insulating characteristics, although yarns of polypropylene, 100% wool, or wool blends may be used. It has ben found that for optimum performance, a one-by-one rib knit stitch pattern in a sport or worsted weight yarn of acrylic fiber provides the best combination of inherent elasticity or stretchability and heat insulating properties. To provide greater elasticity, elastic yarn, such as spandex, may be laid in the courses of stitch loops in the top portion as well as in other portions of the knit cover.

Along with being limited to the acrylic knits, Curtis is silent regarding any assistance with the development of an infant's visual acuity or the transfer of the mother's scent to an infantile environment.

14) U.S. Pat. No. 3,065,944—Libendorfer enables a nursing bottle holder. Among other things, the Libendorfer tubular bottle holder includes a securing ribbon, snaps, heat insulating material and a nylon layer. The '944 device is not intended to be worn inside the mother's undergarment; rather, the Libendorfer device is to be worn about the neck and on the outside of the mother's clothing. The '944 Patent is silent regarding any assistance with the development of an infant's visual acuity or the transfer of the mother's scent to an infantile environment.

15) U.S. Pat. No. 2,522,381—Kramer enables a temperature retaining cover for baby bottles and other receptacles. The Kramer baby bottle hood includes three layers of material with an insulator sandwiched between the two outer layers of fabric and a draw string. The '381 Patent is silent regarding any assistance with the development of an infant's visual acuity or the transfer of the mother's scent to an infantile environment.

16) U.S. Pat. No. 1,669,061—Meltzer enables a combined heat insulator and protector for milk bottles and the like. Meltzer enables a bag-like structure for a baby bottle that includes an outer casing and insulator, an inner pad and binding tapes (18) or ties. The '061 Patent is silent regarding any assistance with the development of an infant's visual acuity or the transfer of the mother's scent to an infantile environment.

17) The Enfamil® Family of Formulas™ Baby Book© 1997, Mead Johnson & Company. The Mead Johnson soft plastic Baby Book teaches, ". . . black and white patterns are easier for babies to distinguish than colors. While they can see colors, the sharp contrast of black and white holds their attention for longer periods of time." And the soft plastic Baby Book features pages of black patterns on white backgrounds.

SUMMARY OF THE INVENTION

The present device and method of using the device are directed toward assisting the developments of the infant's visual acuity and for transferring the mother's scent to an infantile environment. Infantile environments, include but are not limited to incubators, cradles, infants' car seats, cribs or bassinets. The present invention can be practiced in hospital, home and/or daycare-type surroundings.

Supple fabrics, such as, cottons, silks, or manmade blends that can absorb the scent of the mother are incorporated into the invention. Since the practice of certain embodiments of the present invention require the method to wear the device next to the mother's skin, the supple fabrics are manufactured to feel smooth and soft to the mother's skin. The current device absorbs the mother's scent when placed in proximity with the mother's skin, and generally, the mother will wear the apparatus inside or underneath an undergarment to absorb the mother's scent. Based on experimental testing, it has been determined that methods frequently find insertion of the apparatus into the cup of the bassier provides for adequate absorption of the mother's scent as well as ease of use.

Supple fabrics used to practice the present invention have a breadth of no greater than 9 millimeters, preferably 1-6 millimeters, and will adequately absorb a transferable portion of the mother's scent, after a relatively short exposure to the mother's skin. Before assimilating the apparats into the infantile environment, the mother can wear the device for about three hours; however, the current invention is also functional, if the it is placed next to the mother's skin for more or for less than three hours. To lessen the any potential occurrence of fabric bulking, devices practice in accordance with select embodiments of the present invention have a perimeter of 75 centimeters or less.

After the current invention has been entered into the infantile environment, the infant can visualize the highly contrasted colors of the device as well as be exposed to the mother's scent, when the mother is absent. The contrasted colors usable with the present invention are virtually unlimited. However, it has been determined that contrasted black and white patterns are the patterns most preferred by infants.

An aspect the present invention is to provide a device assisting with the development of an infant's visual acuity and for transferring the mother's scent to an infantile environment.

It is another aspect of the present invention to enable a method for assisting the development of the infant's visual acuity and for transferring the mother's scent to the infantile environment.

Still another aspect of the present invention is to provide a device including highly contrasted patterns for stimulating the infant's visual acuity.

Yet another aspect of the present invention is to provide embodiments including highly contrasted geometric patterns for stimulating the infant's visual acuity.

Still another aspect of the present invention is to provide embodiments having a supple fabric for absorbing a portion of the mother's scent to be transferred to the infantile environment.

It is another aspect of the present invention to enable a device that can be fitted onto a nursing bottle.

Yet another aspect of the present invention is to provide a collapsible device that can be expanded to fit over a portion of a nursing bottle.

An embodiment of the present invention can be described as a device for assisting development of an infant's visual acuity and for transferring a mother's scent to an infantile environment, comprising: a collapsible cylinder of supple fabric for contacting said mother's skin underneath an undergarment for absorbing said mother's scent, wherein the collapsible cylinder further comprises: an outward side having at least two contrasting colors and an expandable inward side for abutting an object.

Another embodiment of the present invention can be described as a method for assisting development of infant's visual acuity and for transferring a scent of a mother to an infantile environment, comprising the steps of: arranging contrasting colors about a side of a supple fabric; creating a supple collapsible cylinder having an outward side displaying said contrasting colors; attaching a first elastic about the supple collapsible cylinder; wearing the supple collapsible cylinder next to the mother's skin; fitting the supple collapsible cylinder on to a nursing bottle; and locating the supple collapsible cylinder about said infantile environment.

Yet another embodiment of the present device can be described as a device for assisting development of an infant's visual acuity and for transferring a mother's scent to an infantile environment, comprising: a smooth collapsible cylinder of supple fabric for contacting the mother's skin, wherein said collapsible further comprises: an outward side having at least two contrasting colors; an elastic about a first opening; and a resilient member about a second opening.

It is the novel and unique interaction of these simple elements which creates the methods, within the ambit of the present invention. Pursuant to Title 35 of the United States Code, descriptions of preferred embodiments follow. However, it is to be understood that the best mode description do not limit the scope of the present invention.

DESCRIPTION OF THE PREFERRED EMBODIMENTS

Although the disclosure hereof is detailed to enable those skilled in the art to practice the invention, the embodiments published herein merely exemplify the present invention.

Figure 1:
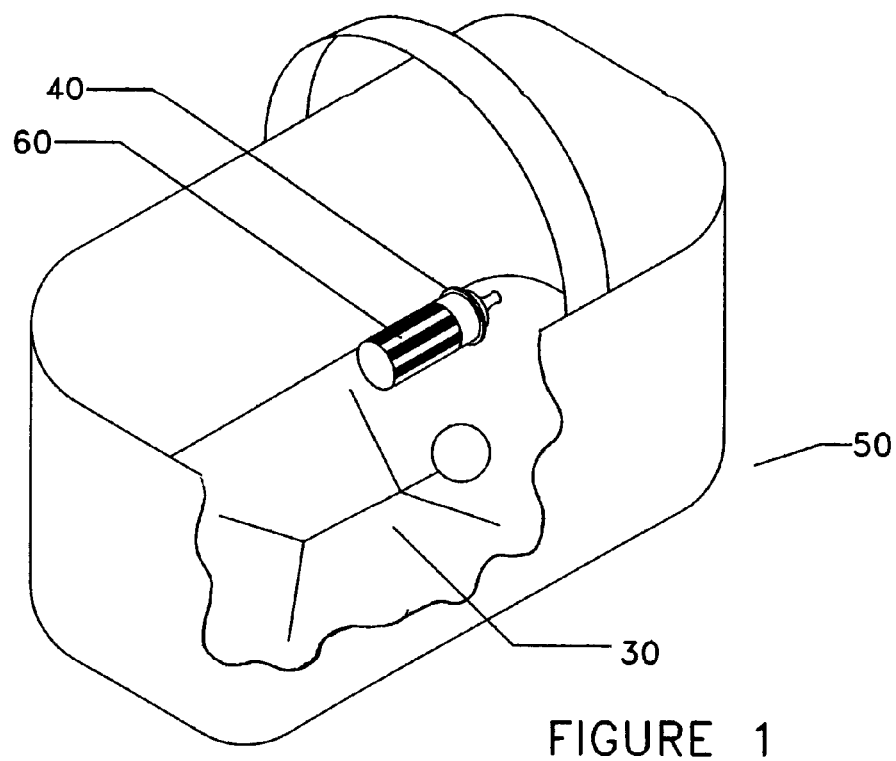
FIG. 1 is a view of an infantile environment, within the scope of the present invention.

FIG. 1 portrays an infantile environment (50), such as incubators, cradles, infants' car seats, cribs, bassinets or the like. As shown, infant (30) is contained within infantile environment (50). Nursing bottle (40) utilizing sleeve (60) of the present invention accompanies infant (30).

Figure 2:
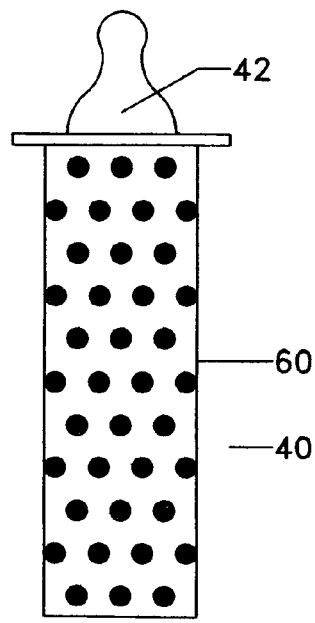
FIG. 2 is a frontal view of a nursing bottle, within the scope of the present invention.
Figure 3:
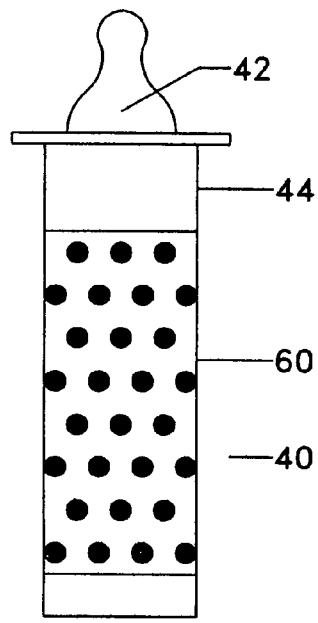
FIG. 3 is a frontal view of a nursing bottle, within the scope of the present invention.

FIGS. 2 and 3 are frontal views of nursing bottle (40). In the FIG. 2 embodiment, due to sleeve (60), only nipple (42) of nursing bottle (100) can be seen because sleeve (60) covers the remainder of the nursing bottle. With a view toward the embodiment of FIG. 3, container (44), nipple (42) of nursing bottle (40) and sleeve (60) are portrayed. As shown in FIG. 3, sleeve (60) covers only a portion of container (44)—allowing the contents of container (44) to be viewed. Depending upon engineering parameters and the sizes of the nursing bottles to be fitted with the present invention, embodiments of sleeve (60) can have variable lengths and variable diameters. For example, certain embodiments of sleeve (60) can have lengths of about 15 centimeters of less and expanded diameters of about 8 centimeters or less.

Figure 4:
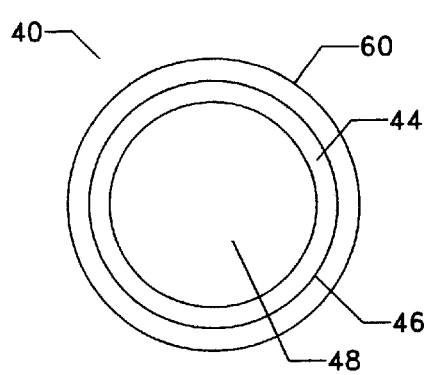
FIG. 4 is a view of the bottom of a nursing bottle utilizing an embodiment of the present invention.

FIG. 4 portrays an embodiment of a view looking towards the bottom of container (44) of nursing bottle (40). Sleeve (60) abuts outward surface (46) of container (44) but does not cover bottom (48) of nursing bottle (40). The practice of this embodiment allows the contents of nursing bottle (40) to be viewed though bottom (48), e.g., when the bottle is turned upside down to feed infant (30).

Figure 5:
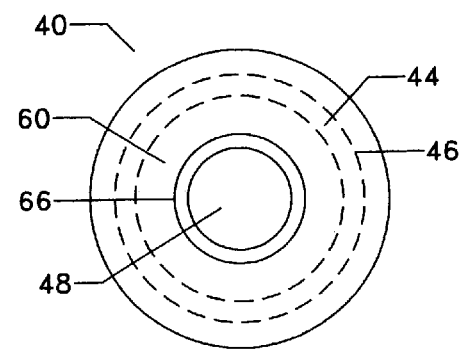
FIG. 5 is a view of the bottom of a nursing bottle utilizing another embodiment of the present invention.

FIG. 5 depicts another embodiment of a bottom view of container (44) (shown in phantom) of nursing bottle (40) utilizing the present invention. Sleeve (60) abuts outward surface (46) (shown in phantom) of container (44) and also covers a portion of bottom (48) of nursing bottle (40). Sleeve (60) is provided with elastic band (66). The practice of this embodiment also allows the contents of nursing bottle (40) to be viewed though bottom (48).

Figure 6:
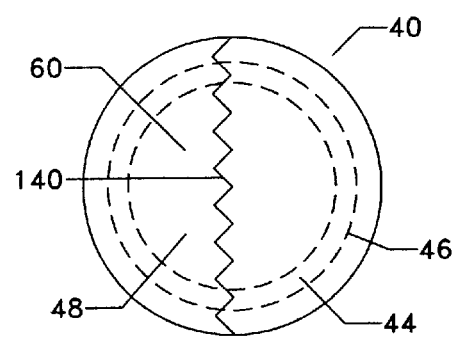
FIG. 6 is a view of the bottom of a nursing bottle utilizing yet another embodiment of the present invention.

FIG. 6 depicts yet another embodiment of a bottom view of container (44) (shown in phantom) of nursing bottle (40) utilizing the present invention. Sleeve (60) abuts outward surface (46) (shown in phantom) of container (44) and also completely covers bottom (48) of nursing bottle (40). In this embodiment, sleeve (60) includes seam (140) for closing an end of sleeve. The practice of this embodiment does not allow the contents of nursing bottle (40) to be viewed though bottom (48).

Figure 7:
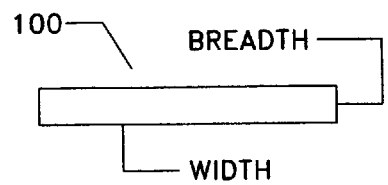
FIG. 7 is a side view of a supple fabric, within the scope of the present invention.
Figure 8:
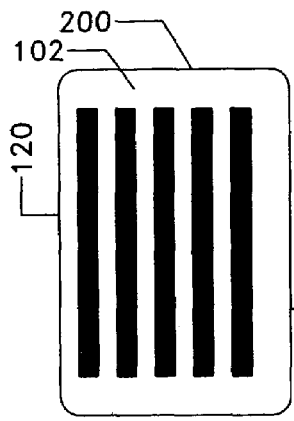
FIGS. 8-14 are laid open views of outward sides of supple fabrics that can be used to create collapsible cylinders, within the scope of the present invention.
Figure 9:
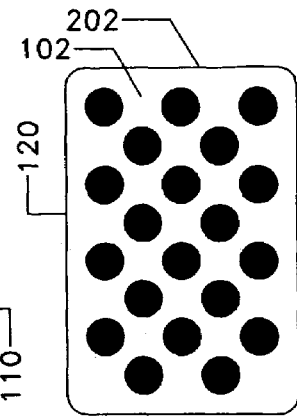
Figure 10:
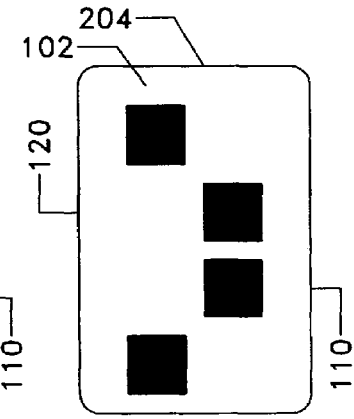
Figure 11:
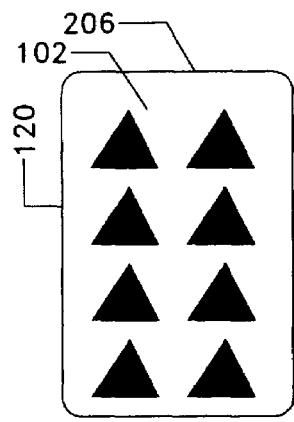
Figure 12:
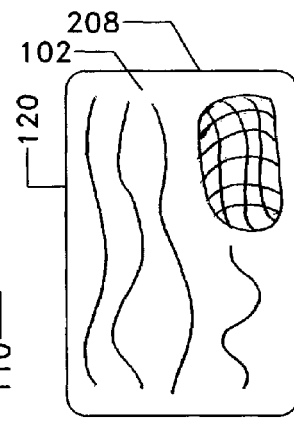
Figure 13:
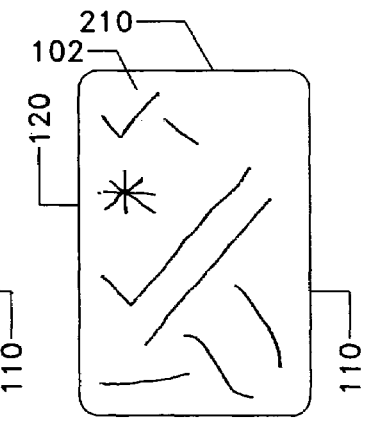
Figure 14:
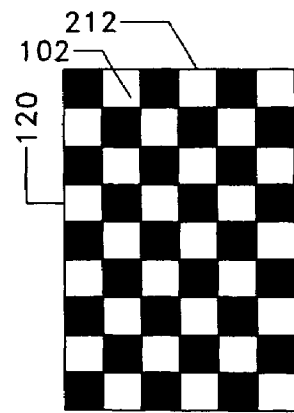

FIG. 7 represents a side view of supple fabric (100) utilized to create sleeve or collapsible cylinder (60), within the scope of the present invention. Supple fabric (100) can have a breadth of from about 1 millimeter to about 6 millimeters.

Supple fabric (100) is composed of cotton, silk or man-made blends that will absorb a portion of the mother's scent. However, it has been determined that various blends of cottons yield better absorption and transference of the mother's scent per square centimeter of fabric. In accordance with the present invention, supple fabrics are soft and smooth to the touch as well as nonirritating to the skin—allowing the mother to wear the supple fabric underneath her undergarments for prolonged periods of time of twelve to twenty-four hours or more. It is suggested that he mother contact her skin with the current invention for at least three hours to absorb a portion of the mother's scent that can thereafter be transferred to the infantile environment. However, supple fabrics of the current invention need only contact the mother's skin for a few minutes to be able to absorb a portion of the mother's scent that can be transferred to the infantile environment.

By way of illustration and not limitation, as shown in the laid open views of FIGS. 8-14, in accordance with the present invention, outward side (102) of supple fabric (100) used to create collapsible cylinder (60) can support patterns (200), (202), (204), (206), (208), (210) or (212). Within the scope of the current invention, the possible combinations of contrasted colors for the patterns (200), (202), (204), (206), (208), (210) and (212) are virtually unlimited. However, it has been determined that contrasted black and white patterns are especially useful in the practice of the present invention. Importantly, a virtually unlimited number of patterns can be practiced with the current invention, and those patterns can be either symmetrical (200, 202, 204, 206 and 212) or freehand (208 and 210).

Figure 15:
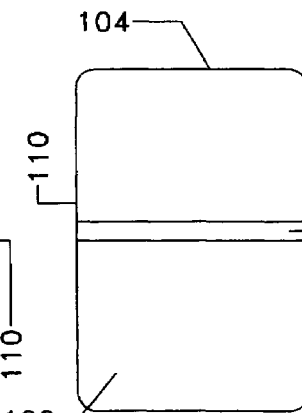
FIGS. 15 and 16 are laid open views of inward sides of supple fabrics that can be used to create collapsible cylinders, within the scope of the present invention.
Figure 16:
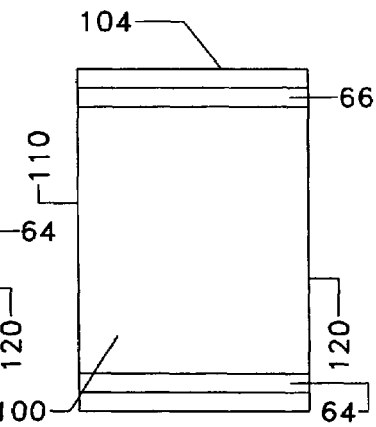

FIGS. 15 and 16 illustrate an laid open view of inward side (104) of supple fabric (100) used to create collapsible cylinder or sleeve (60). Inward side (104) of collapsible cylinder (60) can be of the same pattern as outward side (102), or as portrayed in FIGS. 15 and 16, inward side (104) can be a solid or neutral color. The embodiment disclosed in FIG. 15 shows inward side (104) of collapsible cylinder (60) with a single resilient member (64) while the embodiment disclosed in FIG. 16 portrays inward side (104) of collapsible cylinder including resilient member (64) and elastic (66). Those skilled in the art recognize, resilient member (64) and elastic (66) can be bands formed from the identical elastomeric substance. Resilient member (64) or elastic (66) can traverse the approximate width of supple fabric (100).

Collapsible cylinder (60) can be created by connecting side (110) with side (120) of supple fabric (100). The connector between side (110) and side (120) can be a seam, or the connector between side (110) and side (120) can be an adhesive, or the connector can be some other means. When sides (110) and (120) are connected to form collapsible cylinder (60), a pattern capable of assisting with the development of infant's (30) visual acuity is displayed on outward side (102) of sleeve (60).

Figure 17:
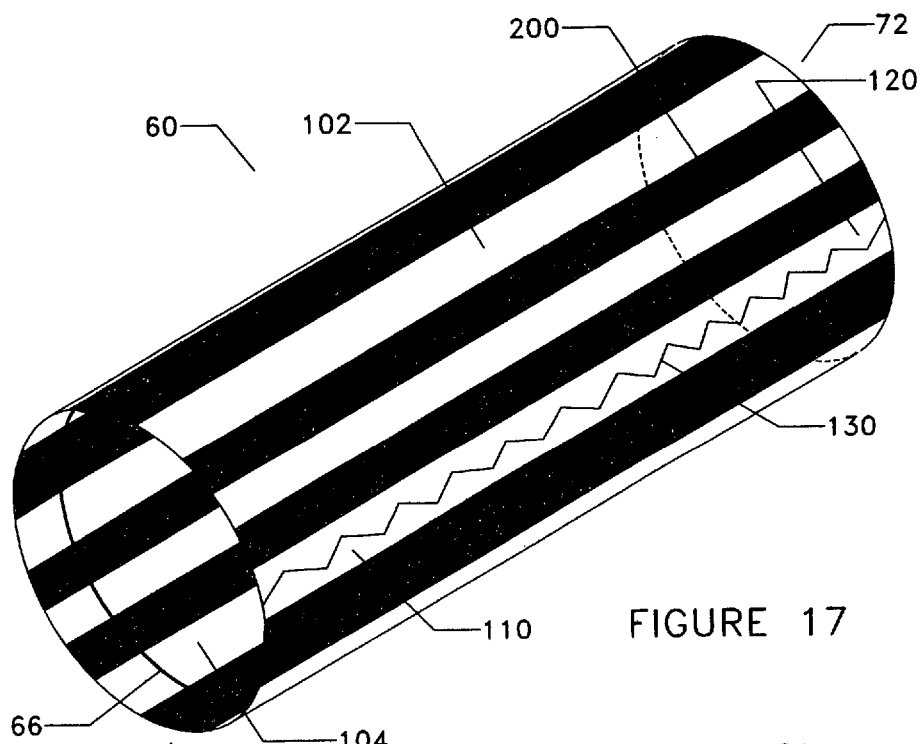
FIG. 17 is a perspective of an embodiment of an expandable collapsible cylinder capable of being fitted about a nursing bottle, within the scope of the present invention.

FIG. 17 discloses an embodiment of an expandable collapsible cylinder (60) capable of being fitted over the container of a nursing bottle (not shown in this view). Threaded seam (130) connects sides (110) and (120) of supple fabric (100) to create collapsible cylinder (60). Supple fabric (100) includes pattern (200) about its outward side (102) and its inward side (104). Expandable collapsible cylinder (60) has first aperture (72) (shown in phantom) and second aperture (74). Elastic (66) is positioned about second aperture (74). Depending on the size of the nursing bottle onto which expandable collapsible cylinder (60) is fitted, at the bottom of nursing bottle (40), second aperture (74) can have variable circumferences such as those portrayed in FIGS. 4 and 5.

Figure 18:
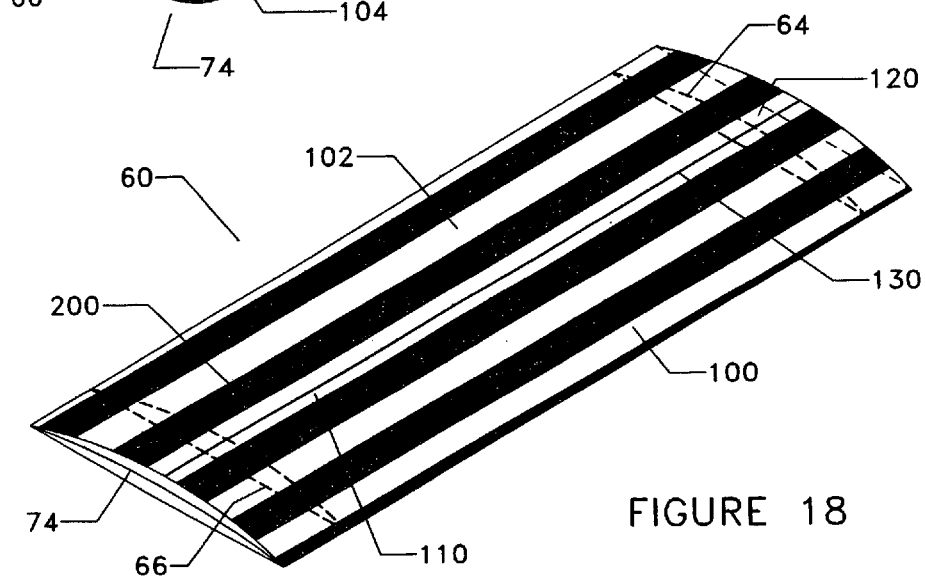
FIG. 18 is a perspective of an embodiment of a collapsed collapsible cylinder, within the scope of the present invention.

FIG. 18 discloses an embodiment of a collapsed collapsible cylinder (60) which is the sleeve's (60) non-fitted state, i.e., when the sleeve is not fitted onto a nursing bottle or other similar object. It is envisioned that the collapsed sleeve (60) embodiment of the present invention is the embodiment that the mother will generally wear underneath an undergarment to absorb a portion of the mother's scent. Adhesive seam (130) connects sides (110) and (120) of supple fabric (100) to create collapsible cylinder (60). Supple fabric (100) includes pattern (200) about its outward side (102). Collapsed collapsible cylinder (60) has a first aperture (not shown) and slit or closed aperture (74). Resilient member (64) and elastic (66) are shown in phantom.

Figure 19:
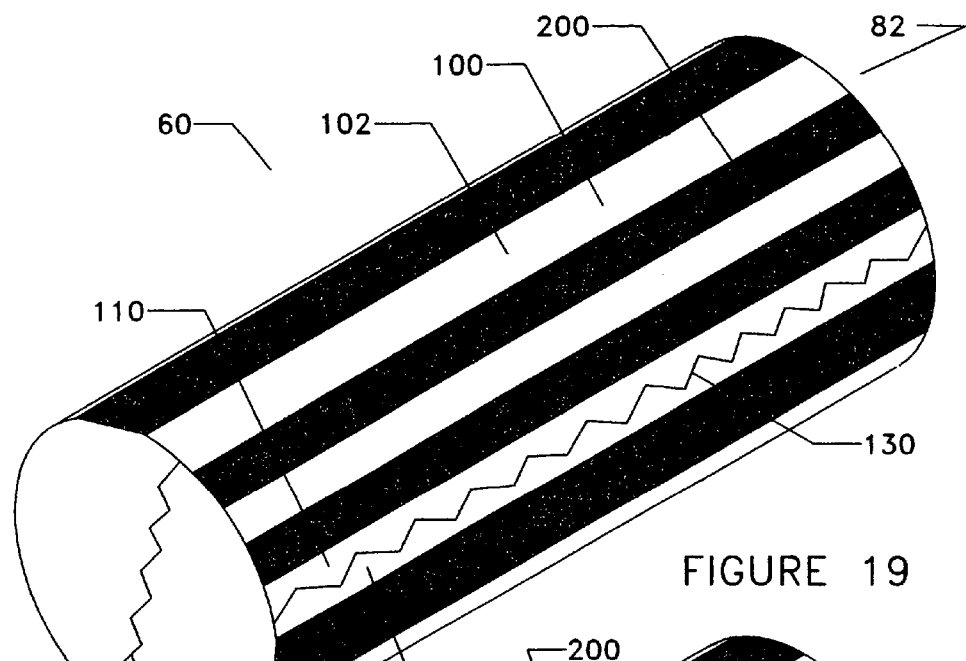
FIG. 19 is a perspective of an embodiment of an expanded sleeve with a closed end, within the scope of the present invention.
Figure 20:
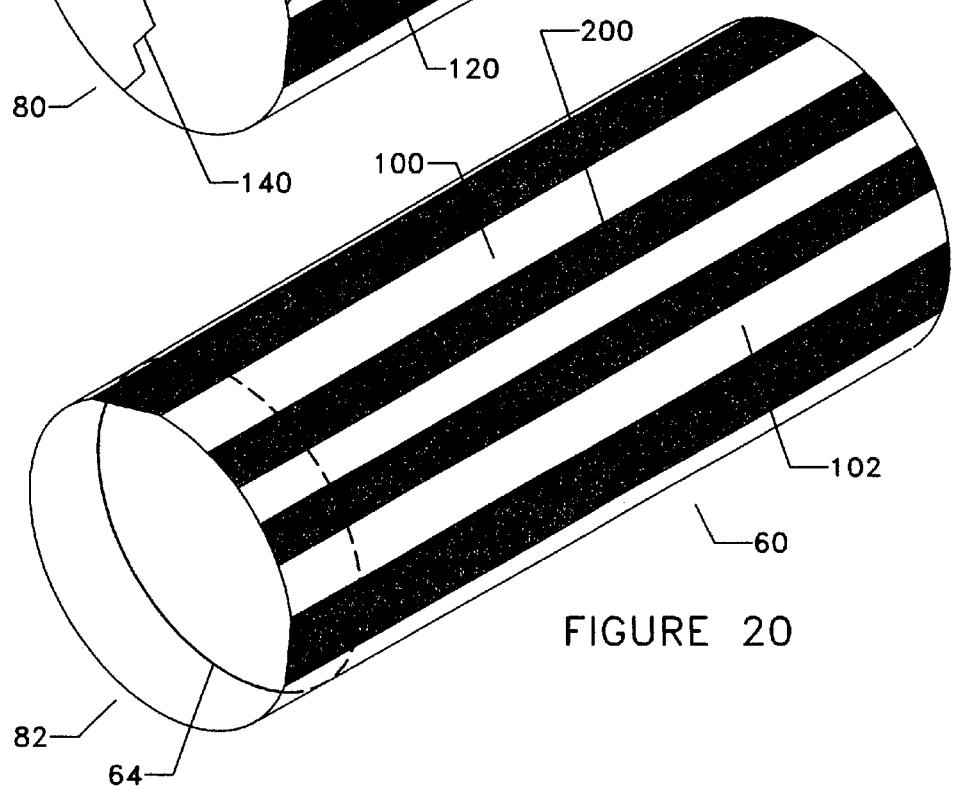
FIG. 20 is a perspective of an open end of the embodiment portrayed in FIG. 19.
Figure 21:
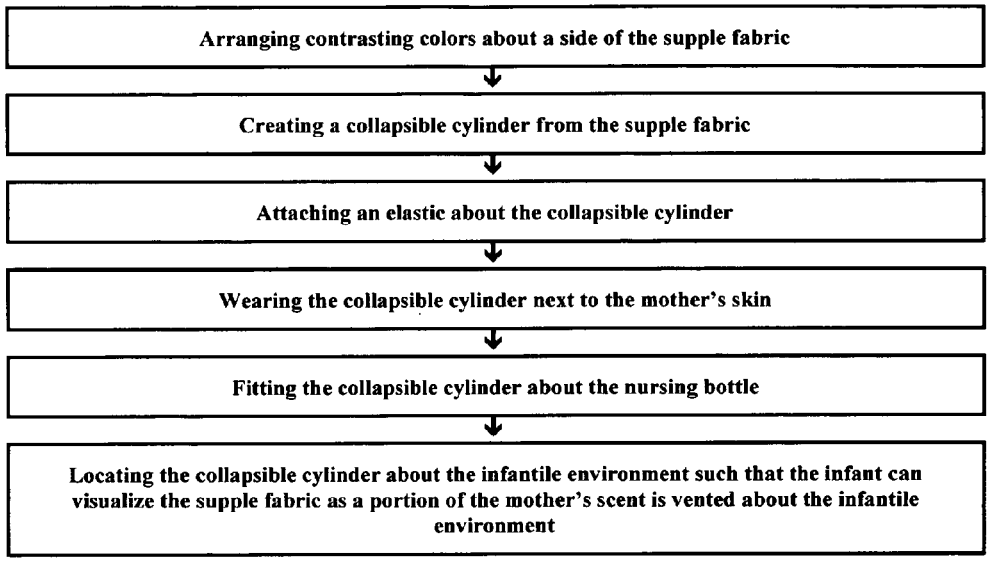
FIG. 21 is an illustration of the steps of an embodiment of the present method.
Figure 22:
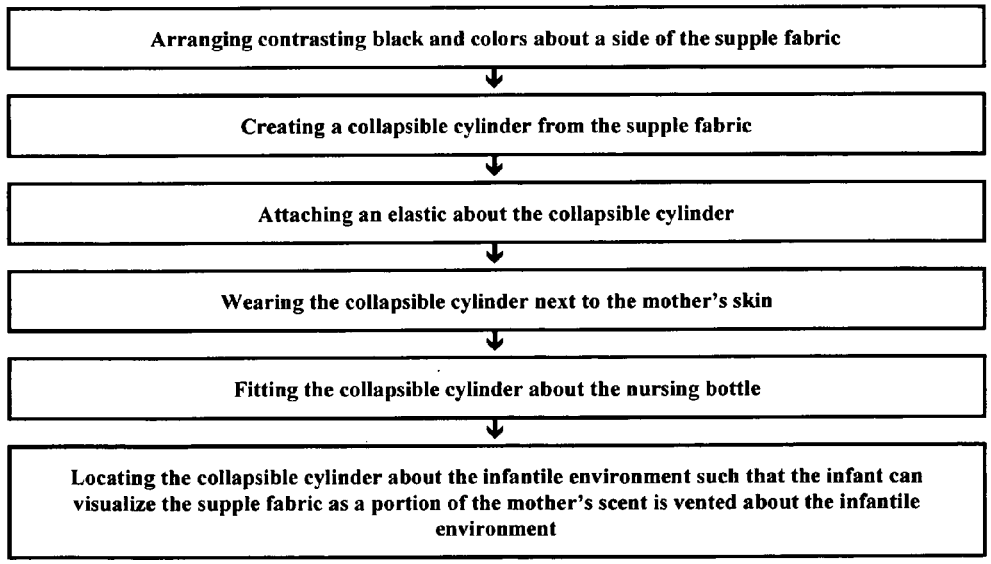
FIG. 22 is a depiction of the steps of another embodiment of the present invention.
Figure 23:
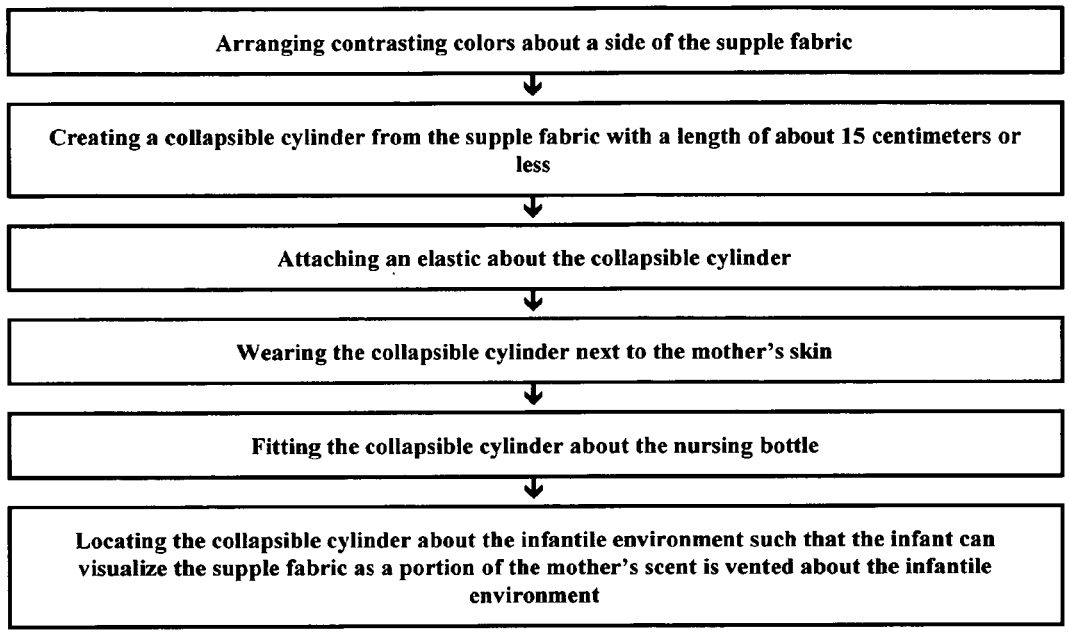
FIG. 23 is an exemplification of the steps of yet another embodiment of the current method.
Figure 24:
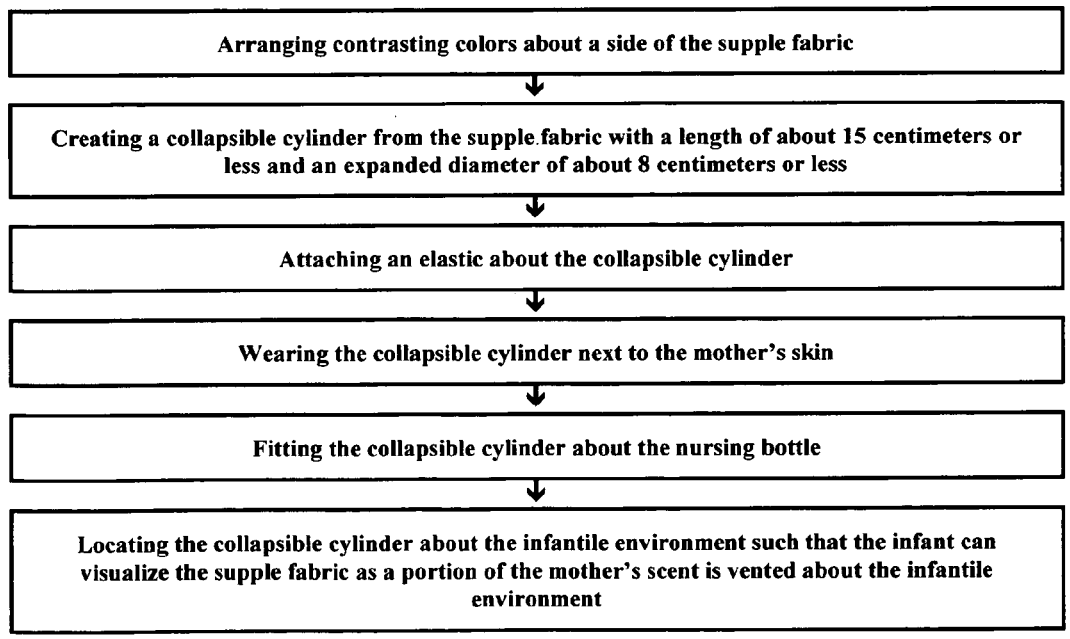
FIG. 24 is yet another illustration of the steps of another embodiment of the present method.

FIG. 19 discloses an embodiment of an expanded sleeve (60) having a closed end (80) and open end (82). Threaded seam (140) closes open end (80) of expanded collapsible cylinder (60). Supple fabric (100) includes pattern (200) about its outward side (102). Threaded seam (130) connects sides (110) and (120) of supple fabric (100) to create collapsible cylinder (60). Resilient member (64) is positioned about open end (82). FIG. 20 portrays open end (82) of expanded sleeve (60).

Steps associated with the methods of practicing the present invention are depicted in FIGS. 21-24.

Regarding the embodiments disclosed herein, locating the supple fabrics or devices in proximity to the infantile environment vents the mother's scent about the infantile environment while also exposing the infant to the contrasted patterns believed to assists in the development of the infant's visual acuity. In accordance with the present invention, both the infant's visual and olfactory senses are stimulated.

Having disclosed the invention as required by Title 35 of the United States Code, Applicants now pray respectfully that Letters Patent be granted for their invention in accordance with the scope of the claims appended hereto.

What is claimed is:

1. A device for assisting development of an infant's visual acuity and for transferring a mother's scent to an infantile environment, comprising:
   a) a collapsible cylinder of supple fabric for contacting said mother's skin underneath an undergarment for absorbing said mother's scent, wherein said collapsible cylinder further comprises:
      i) an outward side having at least two contrasting colors for assisting development of said infant's visual acuity;
      ii) an expandable inward side for abutting an object; and
      iii) a first elastic about said collapsible cylinder.

2. The invention of claim 1, wherein said first elastic is about a first end of said collapsible cylinder.

3. The invention of claim 2 further comprising a resilient member about a second end of said collapsible cylinder.

4. The invention of claim 3, wherein said supple fabric is cotton.

5. The invention of claim 4, wherein said at least two contrasting colors are black and white.

6. The invention of claim 4, wherein said at least two contrasting colors create a symmetrical pattern.

7. A method for assising development of infant's visuals acuity and for transferring a scent of a mother to an infantile environment, comprising the steps of:
   a) arranging contrasting colors about a side of a supple fabric,
   b) connecting a first side of said supple fabric with a second side of said fabric, thereby creating a supple collapsible cylinder having a first opening at a first end, a second opening at a second end and an outward side displaying said contrasting colors;
   c) attaching a first elastic about said supple collapsible cylinder;
   d) wearing said supple collapsible cylinder next to said mother's skin;
   e) transferring said supple collapsible cylinder from said mother and fitting said supple collapsible cylinder on to a nursing bottle; and
   f) locating said supple collapsible cylinder about said infantile environment such that said infant can visualize said supple fabric as a portion of said mother's scent is vented about said infantile environment.

8. The method of claim 7 further comprising the step of sizing said supple collapsible cylinder such that said collapsible cylinder can be easily worn underneath said mother's undergarment.

9. The method of claim 8, wherein said step of arranging contrasting colors about a side of a supple fabric utilizes the colors of black and white.

10. The method of claim 9, wherein said collapsible cylinder is sized to have length of about 15 centimeters or less.

11. A device for assisting development of an infant's visual acuity and for transferring a mother's scent to an infantile environment, comprising:
   a) a smooth collapsible cylinder of supple fabric for contacting said mother's skin underneath an undergarment for absorbing said mother's scent, wherein said smooth collapsible cylinder further comprises:
      i) an outward side having at least two contrasting colors for assisting development of said infant's visual acuity;
      ii) a first opening at a first end of said smooth collapsible cylinder;
      iii) a second opening at a second end of said smooth collapsible cylinder;
      iv) an elastic about said first opening; and
      v) a resilient member about said second opening.

12. The invention of claim 11, wherein said smooth collapsible cylinder further comprises: an expandable inward side for abutting a nursing bottle.

13. The invention of claim 12, wherein said smooth collapsible cylinder includes cotton.

14. The invention of claim 13, wherein said at least two contrasting colors are black and white.

15. The invention of claim 14, wherein said at least two contrasting colors create a symmetrical pattern.

16. The invention of claim 14, wherein said smooth collapsible cylinder has a length of about 15 centimeters or less.

* * * * *